(12) United States Patent
Cole

(10) Patent No.: US 10,434,307 B2
(45) Date of Patent: Oct. 8, 2019

(54) METHODS AND DEVICES FOR SUBCUTANEOUS LEAD IMPLANTATION

(71) Applicant: Medtronic, Inc., Minneapolis, MN (US)

(72) Inventor: Mary L. Cole, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 509 days.

(21) Appl. No.: 14/177,424

(22) Filed: Feb. 11, 2014

(65) Prior Publication Data

US 2015/0105793 A1  Apr. 16, 2015

Related U.S. Application Data

(60) Provisional application No. 61/890,971, filed on Oct. 15, 2013.

(51) Int. Cl.
| | |
|---|---|
| *A61B 17/34* | (2006.01) |
| *A61N 1/05* | (2006.01) |
| *A61N 1/39* | (2006.01) |
| *A61B 17/32* | (2006.01) |
| *A61B 5/046* | (2006.01) |
| *A61M 25/01* | (2006.01) |
| *A61N 1/362* | (2006.01) |

(52) U.S. Cl.
CPC .......... *A61N 1/059* (2013.01); *A61N 1/0504* (2013.01); *A61N 1/3956* (2013.01); *A61B 5/046* (2013.01); *A61B 17/3468* (2013.01); *A61B 2017/320056* (2013.01); *A61M 25/0194* (2013.01); *A61N 1/362* (2013.01)

(58) Field of Classification Search
CPC .... A61B 17/3468; A61B 2017/320056; A61N 1/05; A61M 25/0194
USPC ......................................................... 606/129
See application file for complete search history.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |
| 4,270,549 A | 6/1981 | Heilman |

(Continued)

FOREIGN PATENT DOCUMENTS

| | | |
|---|---|---|
| EP | 0 517 494 A2 | 12/1992 |
| WO | WO 97/20530 | 6/1997 |

(Continued)

OTHER PUBLICATIONS (PCT/US2014/060265) PCT Notification of Transmittal of the International Search Report and the Written Opinion of the International Searching Authority.

(Continued)

*Primary Examiner* — Katrina M Stransky
*Assistant Examiner* — Lindsey Bachman

(57) ABSTRACT

Devices and implantation methods utilizing subcutaneous placement into a patient are disclosed for the insertion, advancement and positioning of a subcutaneous implantable medical device (SIMD) such as a medical electrical lead. The SIMD is releasably-engaged with a device in accordance with embodiments of this disclosure, and advanced from an incision of the patient to an implant location. The implantation device may be disengaged from the SIMD without moving the SIMD from the implant location.

27 Claims, 8 Drawing Sheets

(56) References Cited

U.S. PATENT DOCUMENTS

| | | | |
|---|---|---|---|
| 4,280,510 | A | 7/1981 | O'Neill |
| 4,291,707 | A | 9/1981 | Heilman et al. |
| 4,424,818 | A | 1/1984 | Doring et al. |
| 4,437,475 | A | 3/1984 | White |
| 4,471,777 | A * | 9/1984 | McCorkle, Jr. ...... A61B 17/221 |
| | | | 294/100 |
| 4,512,351 | A | 4/1985 | Pohndorf |
| 4,538,624 | A | 9/1985 | Tarjan |
| 4,644,957 | A | 2/1987 | Ricciardelli |
| 4,765,341 | A | 8/1988 | Mower et al. |
| 4,832,687 | A | 5/1989 | Smith, III |
| 5,036,854 | A | 8/1991 | Schollmeyer et al. |
| 5,125,904 | A | 6/1992 | Lee |
| 5,176,135 | A | 1/1993 | Fain et al. |
| 5,255,691 | A | 10/1993 | Otten |
| 5,273,053 | A | 12/1993 | Pohndorf |
| 5,300,106 | A | 4/1994 | Dahl et al. |
| 5,312,355 | A | 5/1994 | Lee |
| 5,441,504 | A | 8/1995 | Pohndorf et al. |
| 5,456,699 | A | 10/1995 | Armstrong |
| 5,509,924 | A | 4/1996 | Paspa et al. |
| 5,613,953 | A | 3/1997 | Pohndorf |
| 5,667,514 | A | 9/1997 | Heller |
| 5,671,736 | A | 9/1997 | Pettit et al. |
| 5,690,648 | A * | 11/1997 | Fogarty ................ A61N 1/0587 |
| | | | 128/898 |
| 5,752,937 | A | 5/1998 | Otten et al. |
| 5,779,715 | A | 7/1998 | Tu |
| 5,782,841 | A * | 7/1998 | Ritz .......................... A61N 1/05 |
| | | | 606/1 |
| 5,871,528 | A | 2/1999 | Camps et al. |
| 5,944,732 | A | 8/1999 | Raulerson et al. |
| 5,951,518 | A | 9/1999 | Licata et al. |
| 6,032,079 | A | 2/2000 | KenKnight et al. |
| 6,104,957 | A | 8/2000 | Alo et al. |
| 6,122,552 | A | 9/2000 | Tockman et al. |
| 6,159,198 | A | 12/2000 | Gardeski et al. |
| 6,228,052 | B1 | 5/2001 | Pohndorf |
| 6,324,414 | B1 | 11/2001 | Gibbons et al. |
| 6,415,187 | B1 | 7/2002 | Kuzma et al. |
| 6,436,068 | B1 | 8/2002 | Bardy |
| 6,445,954 | B1 | 9/2002 | Olive et al. |
| 6,544,247 | B1 | 4/2003 | Gardeski et al. |
| 6,605,094 | B1 * | 8/2003 | Mann ................. A61B 17/3401 |
| | | | 606/129 |
| 6,730,083 | B2 | 5/2004 | Freigang et al. |
| 6,733,500 | B2 | 5/2004 | Kelley et al. |
| 6,749,574 | B2 | 6/2004 | O'Keefe |
| 6,770,070 | B1 | 8/2004 | Balbierz |
| 6,772,014 | B2 | 8/2004 | Coe et al. |
| 6,836,687 | B2 | 12/2004 | Kelley et al. |
| 6,866,044 | B2 | 3/2005 | Bardy et al. |
| 6,868,291 | B1 | 3/2005 | Bonner et al. |
| 6,887,229 | B1 | 5/2005 | Kurth |
| 7,001,396 | B2 | 2/2006 | Glazier |
| 7,018,384 | B2 | 3/2006 | Skakoon |
| 7,033,326 | B1 | 4/2006 | Pianca et al. |
| 7,069,083 | B2 | 6/2006 | Finch et al. |
| 7,076,296 | B2 | 7/2006 | Rissmann et al. |
| 7,117,039 | B2 | 10/2006 | Manning et al. |
| 7,195,637 | B2 | 3/2007 | Mika |
| 7,218,970 | B2 | 5/2007 | Ley et al. |
| 7,229,450 | B1 | 6/2007 | Chitre et al. |
| 7,288,096 | B2 | 10/2007 | Chin |
| 7,316,667 | B2 | 1/2008 | Linstrom et al. |
| 7,322,960 | B2 | 1/2008 | Yamamoto et al. |
| 7,369,899 | B2 | 5/2008 | Malinowski et al. |
| 7,389,134 | B1 | 6/2008 | Karicherla et al. |
| 7,450,997 | B1 | 11/2008 | Pinanca et al. |
| 7,499,758 | B2 | 3/2009 | Cates et al. |
| 7,499,759 | B2 | 3/2009 | Cates et al. |
| 7,539,542 | B1 | 5/2009 | Malinowski |
| 7,627,375 | B2 | 12/2009 | Bardy et al. |
| 7,655,014 | B2 | 2/2010 | Ko et al. |
| 7,736,309 | B2 | 6/2010 | Miller et al. |
| 7,736,330 | B2 | 6/2010 | Bardy |
| 7,765,014 | B2 | 7/2010 | Eversull et al. |
| 7,837,671 | B2 | 11/2010 | Eversull et al. |
| 7,846,088 | B2 | 12/2010 | Ness |
| 7,890,191 | B2 | 2/2011 | Rutten et al. |
| 7,930,040 | B1 | 4/2011 | Kelsh et al. |
| 7,983,765 | B1 | 7/2011 | Doan et al. |
| 8,012,127 | B2 | 9/2011 | Lieberman et al. |
| 8,057,486 | B2 | 11/2011 | Hansen |
| 8,060,207 | B2 | 11/2011 | Wallace et al. |
| 8,065,020 | B2 | 11/2011 | Ley et al. |
| 8,066,702 | B2 | 11/2011 | Rittman, III et al. |
| 8,083,754 | B2 * | 12/2011 | Pantages ............ A61B 17/0057 |
| | | | 606/144 |
| 8,090,451 | B2 | 1/2012 | Tyson, Jr. |
| 8,155,755 | B2 | 4/2012 | Flynn et al. |
| 8,157,813 | B2 | 4/2012 | Ko et al. |
| 8,260,436 | B2 | 9/2012 | Gerber et al. |
| 8,271,094 | B1 | 9/2012 | Moffitt |
| 8,280,527 | B2 | 10/2012 | Eckerdal et al. |
| 8,340,779 | B2 | 12/2012 | Harris et al. |
| 8,355,786 | B2 | 1/2013 | Malinowski |
| 8,364,277 | B2 | 1/2013 | Glukhovsky |
| 8,386,052 | B2 | 2/2013 | Harris et al. |
| 8,409,233 | B1 | 4/2013 | Chinn et al. |
| 8,435,208 | B2 | 5/2013 | Bardy |
| 8,442,620 | B2 | 5/2013 | Silipo et al. |
| 8,447,398 | B2 | 5/2013 | Bardy et al. |
| 8,452,421 | B2 | 5/2013 | Thenuwara et al. |
| 8,454,552 | B2 | 6/2013 | Bardy |
| 8,478,424 | B2 | 7/2013 | Tronnes |
| 8,478,426 | B2 | 7/2013 | Baker |
| 2002/0120277 | A1 | 8/2002 | Hauschild |
| 2002/0120294 | A1 | 8/2002 | Kroll |
| 2003/0114908 | A1 | 6/2003 | Flach |
| 2003/0233115 | A1 | 12/2003 | Eversull et al. |
| 2004/0054388 | A1 | 3/2004 | Osypka |
| 2004/0059348 | A1 | 3/2004 | Geske et al. |
| 2004/0064147 | A1 | 4/2004 | Struble |
| 2004/0102829 | A1 | 5/2004 | Bonner |
| 2004/0176781 | A1 | 9/2004 | Lindstrom |
| 2004/0210293 | A1 | 10/2004 | Bardy et al. |
| 2004/0236396 | A1 | 11/2004 | Coe et al. |
| 2005/0049663 | A1 | 3/2005 | Harris et al. |
| 2005/0119680 | A1 | 6/2005 | Dykes |
| 2005/0131505 | A1 | 6/2005 | Yokoyama |
| 2005/0288758 | A1 | 12/2005 | Jones et al. |
| 2006/0041295 | A1 | 2/2006 | Okypka |
| 2006/0116746 | A1 | 6/2006 | Chin |
| 2006/0122676 | A1 | 6/2006 | Ko |
| 2006/0253181 | A1 | 11/2006 | Schulman |
| 2006/0265047 | A1 | 11/2006 | Dorn |
| 2007/0100409 | A1 | 5/2007 | Worley et al. |
| 2007/0173900 | A1 | 7/2007 | Siegel |
| 2007/0208402 | A1 | 9/2007 | Helland et al. |
| 2007/0249992 | A1 | 10/2007 | Bardy |
| 2008/0046056 | A1 | 2/2008 | O'Connor |
| 2008/0132933 | A1 | 6/2008 | Gerber |
| 2008/0132970 | A1 | 6/2008 | Barolat |
| 2008/0208303 | A1 | 8/2008 | Rutten et al. |
| 2008/0243219 | A1 | 10/2008 | Malinowski et al. |
| 2008/0269716 | A1 | 10/2008 | Bonde et al. |
| 2009/0076521 | A1 | 3/2009 | Hansen |
| 2009/0157091 | A1 | 6/2009 | Buysman |
| 2009/0222021 | A1 | 9/2009 | Chang |
| 2009/0259283 | A1 | 10/2009 | Brandt et al. |
| 2009/0264780 | A1 | 10/2009 | Schilling |
| 2010/0016935 | A1 | 1/2010 | Strandberg et al. |
| 2010/0030227 | A1 | 2/2010 | Kast et al. |
| 2010/0030228 | A1 | 2/2010 | Havel |
| 2010/0056858 | A1 | 3/2010 | Mokelke et al. |
| 2010/0094252 | A1 | 4/2010 | Wengreen et al. |
| 2010/0113963 | A1 | 5/2010 | Smits et al. |
| 2010/0125194 | A1 | 5/2010 | Bonner et al. |
| 2010/0137879 | A1 | 6/2010 | Ko et al. |
| 2010/0152747 | A1 | 6/2010 | Padiy |
| 2010/0179561 | A1 * | 7/2010 | Pilarski ............ A61B 17/3468 |
| | | | 606/129 |
| 2010/0217298 | A1 | 8/2010 | Bardy |

(56) References Cited

U.S. PATENT DOCUMENTS

| | | |
|---|---|---|
| 2010/0217301 A1 | 8/2010 | Bardy |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009877 A1 | 1/2011 | Thenuwara et al. |
| 2011/0009933 A1 | 1/2011 | Barker |
| 2011/0022057 A1 | 1/2011 | Eigler et al. |
| 2011/0125163 A1 | 5/2011 | Rutten et al. |
| 2011/0224680 A1* | 9/2011 | Barker ............... A61B 17/3468 606/129 |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu |
| 2012/0209285 A1* | 8/2012 | Barker ............... A61B 17/3468 606/129 |
| 2012/0290057 A1 | 11/2012 | Boling et al. |
| 2013/0103049 A1 | 4/2013 | Bonde |
| 2013/0158564 A1 | 6/2013 | Harris et al. |
| 2013/0238067 A1 | 9/2013 | Baudino |
| 2013/0296879 A1 | 11/2013 | Lazeroms et al. |
| 2014/0012292 A1 | 1/2014 | Stewart |
| 2014/0163655 A1 | 6/2014 | Chitre |
| 2014/0276927 A1 | 9/2014 | Barker |
| 2015/0133951 A1 | 5/2015 | Siefert et al. |
| 2015/0133952 A1 | 5/2015 | Siefert et al. |
| 2015/0133953 A1 | 5/2015 | Siefert et al. |
| 2015/0133954 A1 | 5/2015 | Siefert et al. |

FOREIGN PATENT DOCUMENTS

| | | |
|---|---|---|
| WO | 2001023035 A1 | 4/2001 |
| WO | 2004073506 A2 | 9/2004 |
| WO | WO 2010/045228 A2 | 4/2010 |
| WO | 2013076213 A1 | 5/2013 |

OTHER PUBLICATIONS

Avogadros Lab Supply Inc., Catalog; Scoopula with Beech Wood Handle, can be found on-line at http://wwww.avogadro-lab-supply.com/search.php, accessed Oct. 6, 2013, 1 page.

Bielefeld et al., "Thoracoscopic Placement of Implantable Cardioverter-Defibrillator Patch Leads in Sheep," Circulation; Nov. 1993; vol. 88, No. 5, Part 3; 5 pp.

Bolling et al., "Automatic Internal Cardioverter Defibrillator: A Bridge to Heart Transplantation," Heart Lung Transplantation, Abstract Only, Jul.-Aug. 1991, 1 page.

Cigna et al., A New Technique for Substernal Colon Transposition with a Breast Dissector: Report of 39 Cases, Journal of Plastic, Reconstructive and Aesthetic Surgery, 2006; 59, 4 pp. (Applicant points out, in accordance with MPEP 609.04(a), that the year of publication, 2006, is sufficiently earlier than the effective U.S. filing date, Oct. 15, 2013, so that the particular month of publication is not in issue.).

Damiano, "Implantation of Cardioverter Defibrillators in the Post-Sternotomy Patient," The Annals of Thoracic Surger, 1992; 53: pp. 978-983 (Applicant points out, in accordance with MPEP 609.04(a), that the year of publication, 1992, is sufficiently earlier than the effective U.S. filing date, Oct. 15, 2013, so that the particular month of publication is not in issue.).

Ely, et al., "Thorascoscopic Implantation of the Implantable Cardioverter Defibrillator," Minimally Invasive Techniques: (Can be found on the World Wide Web at http://chestioumal.chestpubs.org on May 6, 2013); dated Jan. 1993; 2 pp.

Frame et al., "Long-Term Stability of Defibrillation Thresholds with Intrapericardial Defibrillator Patches" Pacing and Clinical Electrophysiology, Jan. 1993, Part II, vol. 16, 6 pp.

Harman et al., "Differences in the Pathological Changes in Dogs' Hearts After Defibrillation with Extrapericardial Paddles and Implanted Defibrillator Electrodes," Journal of Pacing and Clinical Electrophysiology, Feb. 1991; vol. 14; Part 2; 5 pp.

Karwande et al., Bilateral Anterior Thoracotomy for Automatic Implantable Cardioverter Defibrillator Placement in Patients with Previous Sternotomy, The Annals of Thoracic Surgery, Oct. 1992; 54(4); 3 pp.

Lawrie, et al., Right Mini-Thoracotomy: An Adjunct to Left Subcostal Automatic Implantable Cardioverter Defibrillator Implantation,: The Annals of Thoracic Surgery; 1989; 47; 4 pp. (Applicant points out, in accordance with MPEP 609.04(a), that the year of publication, 1989, is sufficiently earlier than the effective U.S. filing date, Oct. 15, 2013, so that the particular month of publication is not in issue.).

Lemmer, "Defibrillator Patch Constriction, Letter to the Editor," The Annals of Thoracic Surgery, 1996, 1 pp. (Applicant points out, in accordance with MPEP 609.04(a), that the year of publication, 1996, is sufficiently earlier than the effective U.S. filing date, Oct. 15, 2013, so that the particular month of publication is not in issue.).

Medtronic, Inc. 6996SQ Subcutanesous, Unipolar Lead with Defibrillation Coil Electrode, Technical Manual, 22 pp. (Applicant points out, in accordance with MPEP 609.04(a), that the year of publication, 2012, is sufficiently earlier than the effective U.S. filing date, Oct. 15, 2013, so that the particular month of publication is not in issue.).

Medtronic, Inc. 6996T Tunneling Tool, Technical Manual, 12 pp. (Applicant points out, in accordance with MPEP 609.04(a), that the year of publication, 2011, is sufficiently earlier than the effective U.S. filing date, Oct. 15, 2013, so that the particular month of publication is not in issue.).

Mitchell et al., "Experience with an Implantable Tiered Therapy Device Incorporating Antitachycardia Pacing and Cardioverter/Defibrillator Therapy," Thoracic and Cardiovascular Surgery; Abstract Only, Mar. 1993, 1 pp.

Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pp.

Obadia et al., "Thoracoscopic Approach to Implantable Cardioverter Defibrillator Patch Electrode Implantation," Pacing and Clinical Electrophysiology; Jun. 1996; vol. 19; 6 pp.

Obadia, et al., "New Apporach for Implantation of Automatic Defibrillators Using Videothoracoscopy," Journal Ann Cardiol Angeliol (Paris); Sep. 1994; 43 (7) Abstract Only, 1 pp.

Pebax Product Brochure, accessed on Feb. 28, 2014, from http://www.pebax.com/export/sites/pebax/content/medias/downloads/literature/pebax-product-rang-brouchure.pdf, 14 pp.

Piccione et al., "Erosion of Extrapericardial Implantable Cardioverter Defibrillator Patch Through the Gastic Funds with Fistulous Tract Information," Cardiology in Review; Nov./Dec. 2006; 14, e21-e23 pp.

Quigley et al., "Migration of an Automatic Implantable Cardioverter-Defibrillator Patch Causing Massive Hemothorax," Journal Texas Heart Institue, Nov. 1, 1996; vol. 23, 4 pp.

Shapira et al., A Simplied Method for Implantation of Automatic Cardioverter Defibrillator in Patients with Previous Cardiac Surgery, Pacing and Clinical Electrophysiology, Jan. 1993; Part 1; vol. 16; 6 pp.

Steinke et al., Subepicardial Infarction, Myocardial Impression, and Ventricular Penetration by Sutureless Electrode and Leads, Chest; 70: Jul. 1, 1976, 2 pp.

Tung et al., "Minimal Invasive Extra Cardiac Placement of High Voltage Defibrillator Leads", Poster 3; S200 Abstract, P0-3-4; St. Paul Hospital, Vancouver, British Columbia, Canada, Oct. 2007, 1 pp.

Vyhmeister et al., "Simple Approach for Extrapericardial Placement of Defibrillator Patches via Median Sternotomy," The Annals of Thoracic Surgery; 1994; 57; 4 pp. (Applicant points out, in accordance with MPEP 609.04(a), that the year of publication, 1994, is

(56) References Cited

OTHER PUBLICATIONS sufficiently earlier than the effective U.S. filing date, Oct. 15, 2013, so that the particular month of publication is not in issue.).

* cited by examiner ns and having at least a first crescent-shaped segment, the elongate body having a proximal end and a distal end, a channel defined on an inner surface of the first segment and extending along a length of the first crescent-shaped segment, and an engagement mechanism disposed on the proximal end, the engagement mechanism being configured to releasably engage the lead.

METHODS AND DEVICES FOR SUBCUTANEOUS LEAD IMPLANTATION

CROSS-REFERENCE TO RELATED APPLICATIONS

This application claims the benefit of priority from U.S. Provisional Application No. 61/890,971, filed on Oct. 15, 2013, the content of which is incorporated herein by reference in its entirety.

FIELD

The disclosure relates generally to implantable medical devices of the type for performing monitoring of a physiologic state and/or therapy delivery. In particular, the disclosure pertains to tools for implanting medical electrical leads for the physiologic state monitoring and/or therapy delivery.

BACKGROUND

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the EGM.

The IMDs include implantable pulse generators (IPGs), implantable cardioverter/defibrillators (ICDs), and implantable pacemaker/cardioverter/defibrillators (PCDs). The IMDs provide stimulation at pacing levels, high level stimulation via cardioversion and/or defibrillation, extensive diagnostic capabilities and high speed telemetry systems. Such IMDs are typically implanted into patients who have experienced a significant cardiac event.

Attempts at identifying those patients who are asymptomatic by conventional measures but are nevertheless at risk of a future sudden death episode are being undertaken. Current studies of patient populations, e.g., the MADIT II and SCDHeFT studies, are establishing that there are large numbers of patients in any given population that are susceptible to sudden cardiac death, and that they can be identified with some degree of certainty. One developing option for this patient population is to implant a prophylactic subcutaneous implantable cardioverter/defibrillator (SubQ ICD) to deliver therapy in the event of a cardiac episode, such as sudden cardiac arrest, in order to reduce the risk of death resuming from the episode, and who will then have a full-featured ICD with transvenous leads implanted.

Current implanted subcutaneous coil leads are complicated and time consuming to implant and may dislodge or pull back acutely. Further, fibrosis and tissue build-up make it impossible to remove intracardial leads after a few month of implant.

Therefore, for these and other reasons, a need exists for an improved method and apparatus for a subcutaneously implanted lead that is easy to implant and stays fixed in the proper location acutely and chronically, or until it becomes desirable to remove the lead for repositioning or remove the lead permanent

SUMMARY

A device and method for implantation of a subcutaneous implantable medical device (SIMD) is disclosed. Exemplary devices include an elongate body formed from a resilient material and having at least a first crescent-shaped segment, the elongate body having a proximal end and a distal end, a channel defined on an inner surface of the first segment and extending along a length of the first crescent-shaped segment, and an engagement mechanism disposed on the proximal end, the engagement mechanism being configured to releasably engage the lead.

In accordance with embodiments of this disclosure, the method for placement of an implantable medical lead in a patient's body includes forming a first incision at a first location of the body, providing a tunneling tool having a proximal end, a distal end and a channel extending between the proximal end and the distal end, inserting a first portion of the lead into the first incision, positioning a second portion of the lead within the channel, wherein the tunneling tool is configured such that at least the first portion of the lead is located outside the channel, and guiding the lead from the first location to a second location that is spaced apart from the first location using the tunneling tool.

BRIEF DESCRIPTION OF THE DRAWINGS

Various exemplary embodiments of the compositions and methods according to the invention will be described in detail, with reference to the following figures wherein.

DETAILED DESCRIPTION

This disclosure pertains to devices and methods for implantation of a subcutaneous implantable medical device within a patient, such as in a substernal space. In this disclosure, "substernal space" refers to the region defined by the undersurface between the sternum and the body cavity but not including the pericardium. In other words, the region is dorsal to the sternum and ventral to the ascending aorta. The substernal space may alternatively be referred to by the terms "retrosternal space" or "mediastinum" or "infrasternal" as is known to those skilled in the art and includes the region referred to as the anterior mediastinum. For ease of description, the term substernal space will be used in this disclosure, it being understood that the term is interchangeable with any of the other aforementioned terms.

In this disclosure, the term "extra-pericardial" space refers to region around, but not in contact with, the outer heart surface. The region defined as the extra-pericardial space includes the gap, tissue, bone, or other anatomical features around the perimeter of, and adjacent to, but not in contact with the pericardium.

Figure 1:
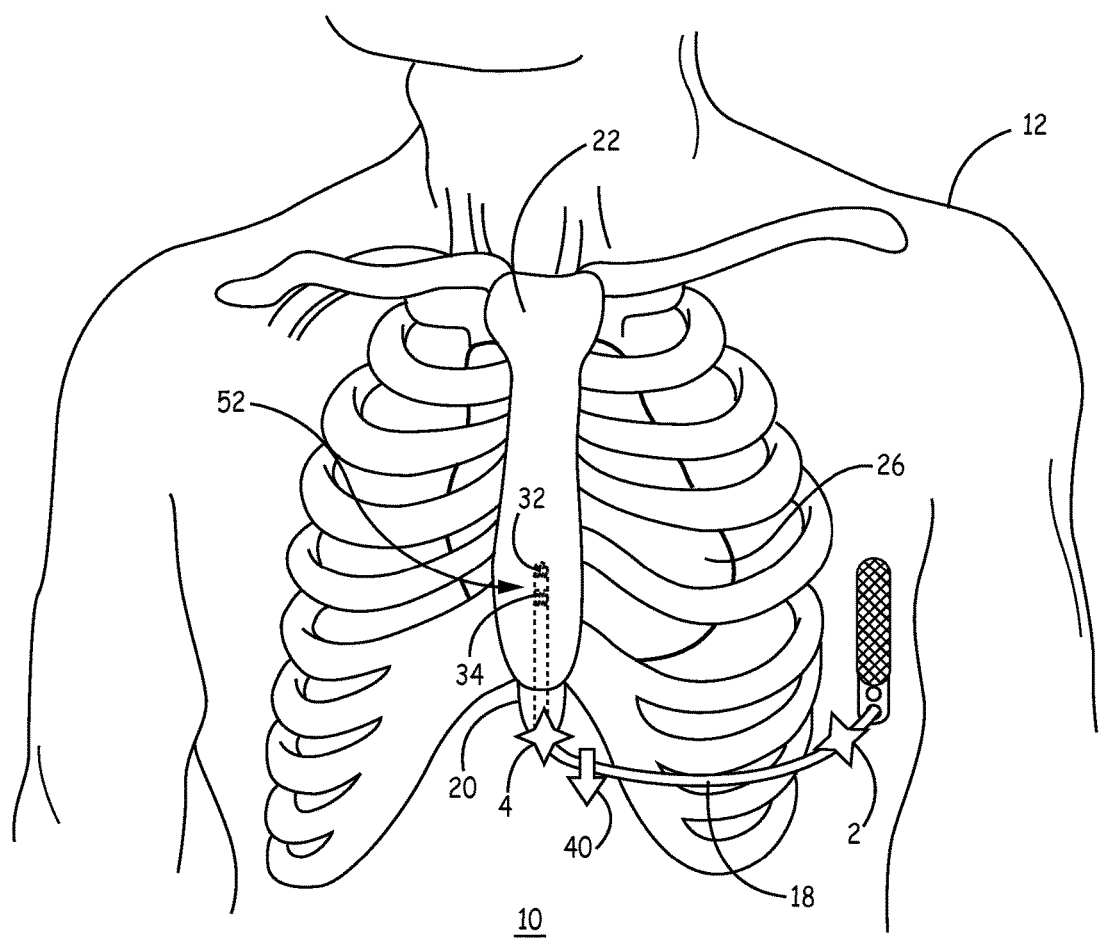
FIG. 1 is a front view of patient implanted with an implantable cardiac system.
Figure 2:
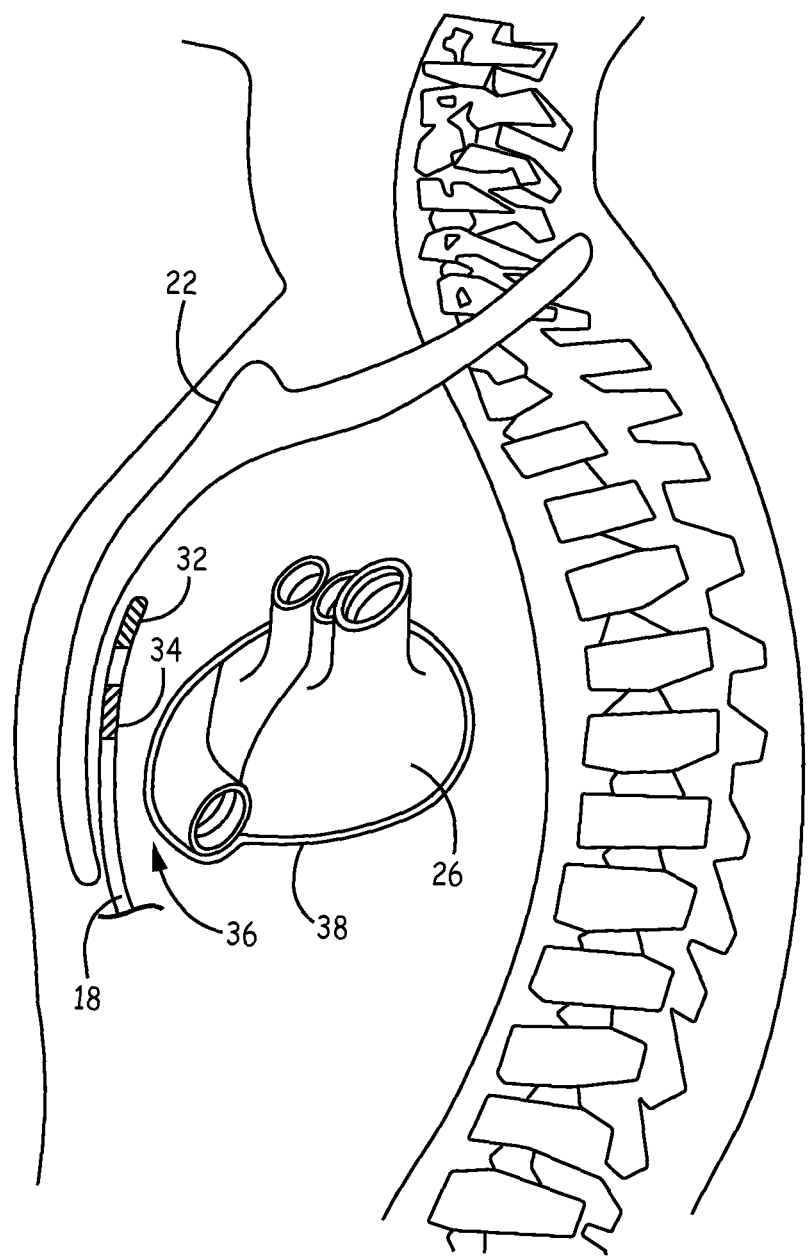
FIG. 2 is a side view of a patient implanted with an implantable cardiac system.

FIGS. 1-2 are conceptual diagrams of a patient 12 implanted with an example implantable cardiac system 10. FIG. 1 is a front view of patient 12 implanted with implantable cardiac system 10. FIG. 2 is a side view patient 12 with implantable cardiac system 10.

Implantable cardiac system 10 includes an implantable cardiac defibrillator (ICD) 14 connected to a lead 18. The lead 18 may be utilized for sensing and/or to provide an electrical stimulation therapy such as pacing or defibrillation. Lead 18 includes electrodes 32 and 34 that may be configured for delivery of the stimulation therapy. In addition, or alternatively, the electrodes 32, 34 may be configured for sensing.

ICD 14 may provide stimulation therapy and/or sense electrical activity of heart 26 via a combination of delivery/sensing vectors that include combinations of electrodes 32 and 34 and the housing or can electrode of ICD 14. For example, ICD 14 may deliver therapy or obtain electrical signals sensed using a delivery/sensing vector between electrodes 32 and 34, or using a delivery/sensing vector between electrode 32 and the conductive housing or can electrode of ICD 14, or using a delivery/sensing vector between electrode 34 and the conductive housing or can electrode of ICD 14, or a combination thereof. In this manner, sensing, defibrillation therapy, ATP therapy or post shock pacing (or other pacing therapy) may be provided in an ICD system without entering the vasculature or the pericardial space, nor making intimate contact with the heart.

The electrodes 32 and 34 may be located near a distal end of lead 18. Electrodes 32 and 34 may comprise ring electrodes, hemispherical electrodes, coil electrodes, helix electrodes, or other types of electrodes, or combination thereof. Electrodes 32 and 34 may be the same type of electrodes or different types of electrodes.

The lead body of lead 18 also includes one or more elongated electrical conductors (not illustrated) that extend through the lead body from the connector assembly of ICD 14 provided at a proximal lead end to electrodes 32, 34. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may engage with respective ones of electrodes 32, 34. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 32, 34 and transmit sensed electrical signals from one or more of electrodes 32, 34 to the sensing module within ICD 14.

In the example illustrated in FIGS. 1-2, ICD 14 is implanted subcutaneously on the left midaxillary of patient 12. ICD 14 may, however, be implanted at other subcutaneous locations on patient 12. The lead 18 may be inserted through an incision 2 or 4 on the patient's body for subcutaneous and/or extrapericardial implantation as will be described in more detail below.

Lead 18 includes a proximal end that is connected to ICD 14 and a distal end that includes one or more electrodes. Lead 18 may be implanted within the mediastinum such that one or more electrodes 32 and 34 are located over a cardiac silhouette of the ventricle as observed via fluoroscopy. In the example illustrated in FIGS. 1-2, lead 18 is located substantially centered under sternum 22. Lead 18 extends subcutaneously from ICD 14 toward xiphoid process 20. At a location near xiphoid process 20 lead 18 bends or turns and extends superior upward in the substernal space. In one example, lead 18 may be placed in the mediastinum 36 and, more particularly, in the anterior mediastinum. The anterior mediastinum is bounded laterally by pleurae 40, posteriorly by pericardium 38, and anteriorly by sternum 22. In other instances, however, lead 18 may be implanted such that it is offset laterally from the center of sternum 22. Alternatively, lead 18 may be placed such that a therapy vector between one of electrodes 32, 34 and a housing or can electrode of ICD 14 is substantially across the ventricle of heart 26. Although described herein as being implanted in the substernal space, the mediastinum, or the anterior mediastinum, lead 18 may be implanted in other extra-pericardial locations.

The configuration described above in FIGS. 1-2 is directed to providing ventricular pacing via lead 18. In situations in which atrial pacing is desired in addition to or instead of ventricular pacing, lead 18 may be positioned further superior. A pacing lead configured to deliver pacing pulses to both the atrium and ventricle may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. In some instances, two substernal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy.

ICD 14 may include a housing that forms a hermetic seal that protects components of ICD 14. The housing of ICD 14 may be formed of a conductive material, such as titanium. ICD 14 may also include a connector assembly (also referred to as a connector block or header) that includes electrical feedthroughs through which electrical connections are made between conductors within lead 18 and electronic components included within the housing. Housing may enclose one or more processors, memories, transmitters, receivers, sensors, sensing circuitry, therapy circuitry and other appropriate components as is known in the art. Housing 34 is configured to be implanted in a patient, such as patient 12.

As shown in FIG. 1, an anchoring mechanism 40 may be provided along the lead body to couple the lead 18 at an access point 4 through which the distal end of the lead 18 is inserted into the substernal space. The access point 4 is any location that provides access into the substernal space. In one exemplary embodiment, the access point 4 is adjacent to or below the xiphoid process (also referred to as "subxiphoid"). The access point may also be at the notch (not shown) that connects the xiphoid process to the sternum. In other embodiments, the substernal space may also be accessed through the manubrium.

The anchoring mechanism 40 is fixedly-coupled to cartilage, musculature, tissue or bone at the entry point into the substernal space at or near the access point at which site the body of the lead 18 transitions from the subcutaneous tissue into the substernal space of patient 12. An example of the anchoring mechanism 40 includes a suture or clip or other fastener that anchors the lead body to the patient 12. Such anchoring mechanism 40 may be coupled directly to the lead body or to a suture sleeve such as that described in U.S. Pat. No. 5,273,053, issued to Pohndorf and incorporated herein by reference in its entirety.

The examples illustrated in FIGS. 1-2 are exemplary in nature and should not be considered limiting of the techniques described in this disclosure. In other examples, ICD 14 and lead 18 may be implanted at other locations. For example, ICD 14 may be implanted in a subcutaneous pocket in the right chest. In this example, lead 18 may be extend subcutaneously from the device toward the manubrium of the sternum and bend or turn and extend subcutaneously inferiorily from the manubrium of the sternum, substantially parallel with the sternum.

In addition, it should be noted that system 10 may not be limited to treatment of a human patient. In alternative examples, system 10 may be implemented in non-human patients, e.g., primates, canines, equines, pigs, and felines. These other animals may undergo clinical or research therapies that may benefit from the subject matter of this disclosure.

Figure 3A:
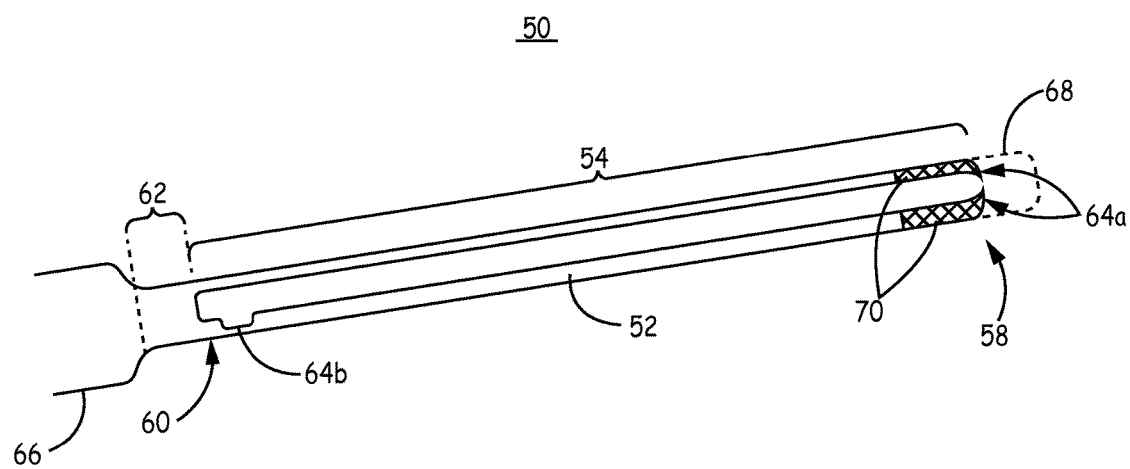
FIGS. 3A-C illustrate cross-sectional views of a tunneling tool in accordance with an embodiment of the disclosure.
Figure 3B:
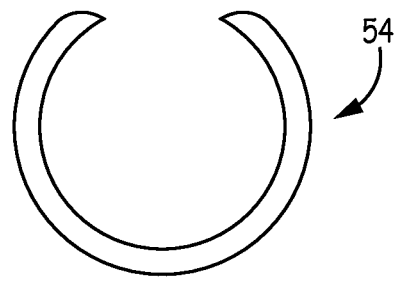
Figure 3C:
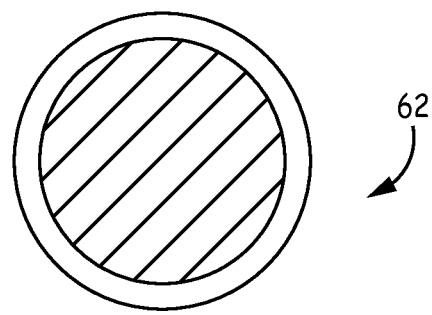

FIGS. 3A-C illustrate a tunneling tool 50 in accordance with an embodiment of the disclosure. FIG. 3A illustrates a cross-sectional side view of the tunneling tool 50. FIGS. 3B and 3C illustrate cross-sectional view of the tunneling tool 50 at the segments 54, and 62, respectively. The tunneling tool 50 facilitates advancement of medical devices such as lead 18, medical tubes, catheters, or other medical devices. For example, the tunneling tool 50 is suited for advancing lead 18 through a subcutaneous location and/or an extra-pericardial space during an implant procedure.

The tunneling tool 50 comprises an elongate body 52 that is coupled to a handle 60. The elongate body 52 includes a crescent-shaped segment 54. An inner surface of the elongate body 52 defines a channel 56 that is configured to receive the lead 18. For example, the crescent-shaped segment 54 defines the channel 56 that extends from a distal end 58 of the elongate body 52 to a proximal portion 60 of the elongate body 52. The elongate body 52 may further include a segment 62 that is formed adjacent to the crescent-shaped segment 54. In the illustrative embodiment, the segment 62 is formed as a cylindrically-shaped segment. However, the segment 62 may alternatively be formed in any other shapes such as the crescent-shaped segment.

The elongate body 52 may further include one or more lead engagement mechanisms 64a, 64b. Collectively, the lead engagement mechanisms 64 are provided for releasably-engaging the lead 18 during a procedure such as to implant the lead 18. The lead 18 may subsequently be disengaged from the lead engagement mechanisms 64 upon successful placement of the lead 18 within the target tissue. In alternative embodiments, the tunneling tool may include an optional tunneling tip 68 (illustrate in phantom lines) at the distal end 58 of the elongate body 52.

The elongate body 52 may further include a radiopaque marker element 70. In the illustrative embodiment, the element 70 is depicted overlaying a distal portion of the elongate body 52. Nevertheless, it should be understood that the element 70 may overlay or coat any other section or sections of the elongate body 52 or may alternatively overlay the entire elongate body 52. Element 70 may be formed from a band of radiopaque material that is coupled to the distal portion through any suitable mechanism. In other embodiments, the distal portion may be formed from a radiopaque material such as polypropylene having about 15% by weight barium sulfate. The material forming element 70 may include a compound, such as barium sulphate, that is visible through a fluoroscopic imaging procedure. In use, the element 70 can provide a visual depiction or image of the elongate body 52.

Elongate body 52 may be formed from a pliable material such as bio-compatible plastic including polyaryletheretherketone (PEEK) thermoplastic, PARYLENE® polyxylylene polymers, or other suitable polymer material. The material may also be selected from a bendable or rigid material, such as materials including metals and metal alloys, such as titanium or stainless steel. In further embodiments, the elongate body 52 may be formed from bio-compatible rigid materials such, for example, as TECOTHANE® thermoplastic polyurethanes that may have elastic "memory".

A handle 66 is coupled to the proximal end of elongate body 52. Handle 66 facilitates maneuvering of the elongate body 52. The handle 66 may be formed from materials similar to those of the elongate body 52 or from a different material.

Figure 4:
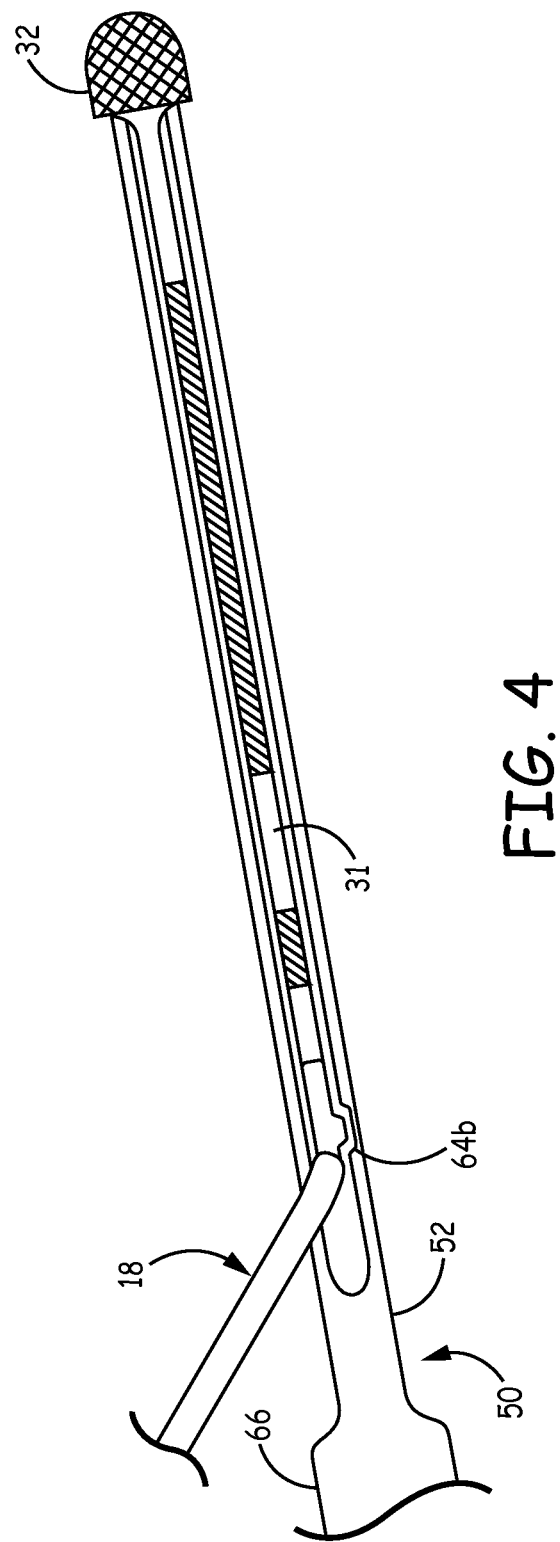
FIG. 4 depicts a tunneling tool in accordance with an embodiment of the disclosure in an illustrative use for advancing a device.

Turning next to FIG. 4, the tunneling tool 50 is shown as it would be used for advancing a device such as lead 18. The body of the lead 18 is shown having a first portion 31 that fits within the channel 56, and a second portion, shown herein as electrode 32, that is exposed outside of the channel 56. The first portion 31 and the channel 56 may be configured with dimensions that enable a friction fit to be formed between the inner wall of the tunneling tool 50 and body of lead 18. With this configuration, the electrode 32 defines a proximal tip that is exposed outside of the tunneling tool such that the electrode 32 will dissect tissue during the implant procedure to create a pathway. As such, the channel 56 is dimensioned to receive and hold in place the first portion 31 of the lead 18, but with the second portion being disposed external to the channel 56. In addition or alternatively, the lead engagement mechanism 64a may suitably be provided to engage the second portion to secure it exteriorly of the channel 56.

In embodiments having tunneling tip 68, the second portion of lead 18 may rest entirely within the tunneling tip 68 so as not to expose the lead 18. This embodiment is particularly suitable for lead 18 constructed with a uniform lead body diameter.

Figure 5:
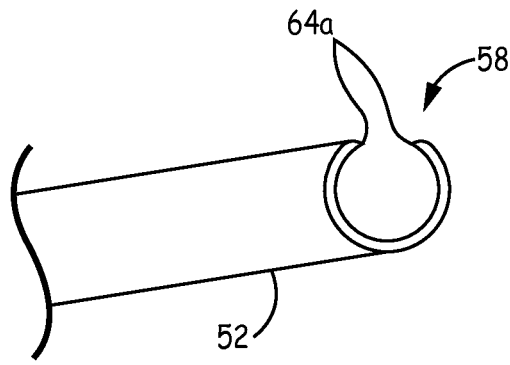
FIG. 5 illustrates a side view of an embodiment of a tunneling tool in accordance with an embodiment of the disclosure.
Figure 6:
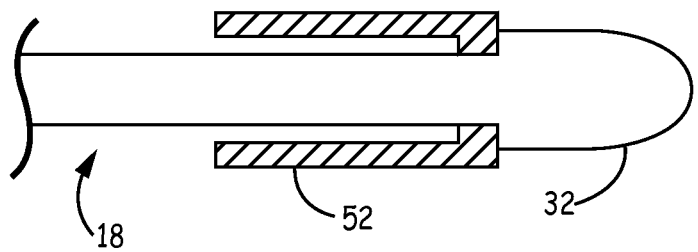
FIG. 6 is a top perspective view of a distal portion of a tunneling tool with a lead disposed therein.
Figure 7:
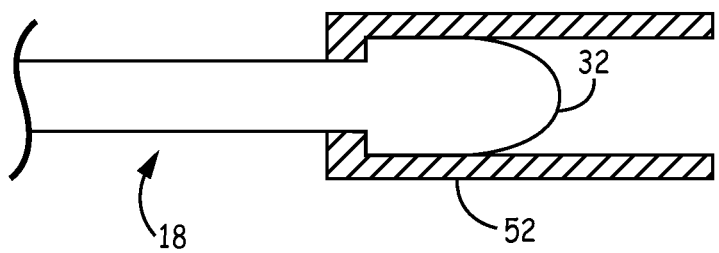
FIG. 7 depicts yet another top perspective view of a distal portion of a tunneling tool with a lead disposed therein in accordance with an alternative embodiment.

FIGS. 5-7 illustrate embodiments of the tunneling tool 52 in one configuration for use with a lead 18. The lead engagement mechanism 64a that formed within the distal end 58 of the elongate body 52 is provided to enable releasable engagement of a portion of the lead 18 (for example, second portion). As depicted in FIG. 5, lead engagement mechanism 64a comprises projections that are formed to define an opening at the distal end 58. The body of lead 18 may be dimensioned having a radius that is configured to engage with the lead engagement mechanism 64a, e.g., with a larger radius relative to the lead engagement mechanism 64a to form a friction fit. Thus, the lead engagement mechanism 64a defines an opening into the channel 56 having a radius that is narrower in relation to the radius of the channel 56. In alternative embodiments, the lead engagement mechanism 64a may comprise a rib that is formed at the distal end 58. In other embodiments, the lead engagement mechanism 64a may be formed as a slot, clip, finger, flange, or in any other construction. Regardless of construction, the embodiments of the lead engagement mechanism 64a are predicated on preventing disengagement of the lead 18 from the tunneling tool 50 during an advancement procedure.

FIG. 6 is a top perspective view of the distal portion of the tunneling tool 52 with lead 18 disposed therein. As depicted in FIG. 6, channel 56 receives first portion 31 of lead 18, while the second portion is disposed externally in relation to the channel 56. In this configuration, the second portion 32 abuts the lead engagement mechanism 64a when first portion 31 of lead 18 is inserted into channel 56. In this embodiment, movement of the tunneling tool 50 in a direction towards the distal end 58 causes the lead 18 to be advanced through tissue. In other words, a force exerted on the proximal portion of the tunneling tool 52 is transferred to the second portion 32 to cause the second portion to dissect tissue and create a tunnel in the patient tissue for placement of the lead 18.

FIG. 7 depicts yet another top perspective view of the distal portion of tunneling tool 52 with an alternate configuration for handling and advancing lead 18. In this embodiment, the second portion of lead 18 is inserted within the channel 56 while the first portion 31 is disposed outside the channel 56. In this configuration, the radius of channel 56 is configured to be equal or substantially equal in comparison to the second portion 32. By substantially equal, this disclosure refers to dimensions that provide for a friction fit to be formed between surfaces, such as the second portion and the inner surface of the channel or that the second portion is dimensioned be loosely disposed within the channel. In this embodiment, lead engagement mechanism 64a grasps the second portion 32 of lead 18 to prevent the lead 18 from disengaging from the channel 56 during an implant procedure.

Figure 8:
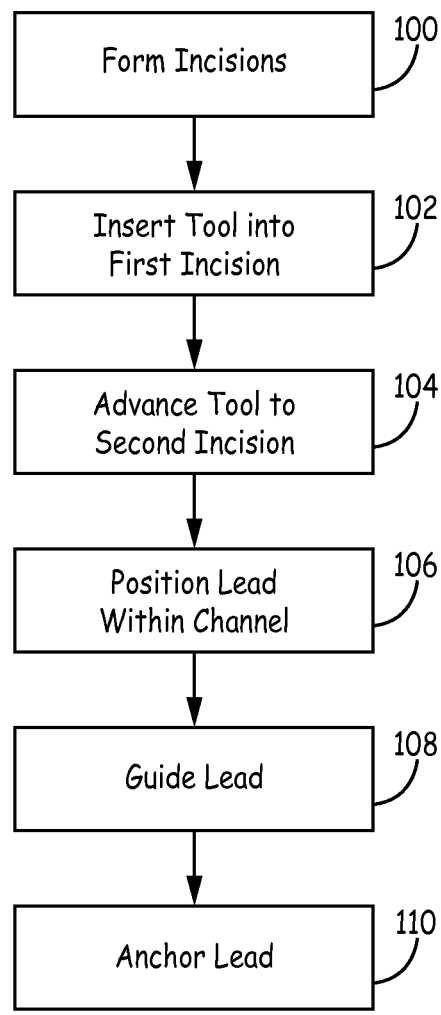
FIG. 8 depicts a flowchart of a method of placing an implantable medical lead in a patient's body.

FIG. 8 depicts a flowchart of a method of placing an implantable medical lead in a patient's body. First incision 2 is made into tissue of the patient and second incision 4 is made in the patient at a location that is spaced apart from the first incision 2 (100). In this embodiment, incision 4 provides the initial point of entry into the patient's body. The initial point of entry of the tunneling tool 50 may be selected based on the desired method of advancing the lead 18 as will be discussed further below. Thus, in this embodiment, tunneling tool 50 is inserted into the incision 4 (102). The tunneling tool 50 is subsequently advanced by manipulating the tool 50 from incision 4 to incision 2 through dissection of the tissue using the distal end of the elongate body 52 to create a tunnel in the patient tissue (104). The dissection of the tissue can be accomplished by feeding tunneling tool 50 into the patient at the entry incision 2. In embodiments where the tunneling tool 50 includes tunneling tip 68, the tip 68 dissects the patient tissue to create the tunnel. Otherwise, the distal end of the tunneling tool 52 will perform the function of dissecting the patient tissue.

After the distal portion of tunneling tool 50 reaches incision 2, at least a portion of the lead is inserted within the channel 56 (106). For example, the second portion 32 is positioned within the channel 56 such that the first portion 31 is located outside the channel 56 as depicted in FIG. 7. The second portion 32 may be releasably engaged within the channel 56, for example using the engagement mechanism 64a. With at least a section of the lead 18 seated within the channel 58, the lead 18 is guided from the incision 2 to incision 4 (108). This may be accomplished by pulling the handle 66 or proximal portion of the tunneling tool 50 such that the distal portion of the tunneling tool 50 is drawn back through the tunnel in a direction from incision 2 to incision 4. The retraction of the tunneling tool 50 guides the lead 18, held within the channel 56, through the tunnel created in the tissue. Hence, the lead 18 is positioned within the tunnel and left therein. Subsequent to placement, the lead 18 may be anchored at one or more locations within the tissue of the patient if it is adjacent to the target tissue (110). The anchoring may be performed through an anchor on the lead 18 that engages cartilage, bone, fascia, muscle or other tissue of patient or simply by wedging the lead 18 in the patient for fixation to prevent excessive motion or dislodgment.

Figure 9:
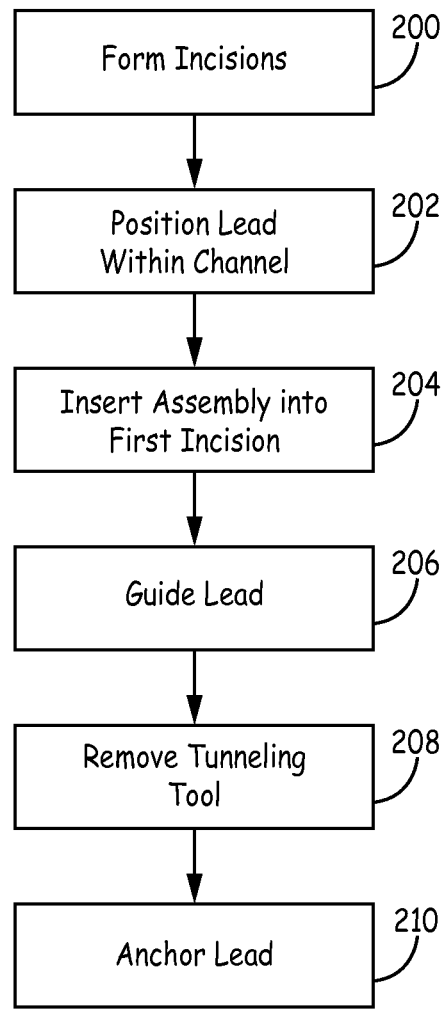
FIG. 9 is a flowchart illustrating a method for placing an implantable medical lead in a patient's body in accordance with an alternative embodiment.

FIG. 9 is a flowchart illustrating a method for placing an implantable medical lead in a patient's body in accordance with an alternative embodiment. A first incision 2 and a second incision 4 are formed on the patient (200). The lead 18 is positioned within the channel 56 (202). The positioning of the lead 18 may be as depicted for example in FIG. 6 where the first portion 31 is disposed within the channel 56 and the second portion 32 is disposed on the exterior of the channel 56.

The second portion of the lead 18 may then be inserted into the incision 2 (204). Next, the lead 18 is guided through the patient tissue (206). In other words, the combination of the tunneling tool 50 and the lead 18 are navigated through the tissue. As depicted in FIG. 6, the second portion 32 is disposed on the exterior of the elongate body 52 and dissects the patient's tissue to form a tunnel from the first incision 2 to the second incision 4. The combination of the lead 18 and tunneling tool 50 are advanced through the tunnel formed by the second portion 32.

After the lead 18 is navigated to incision 4, the first portion 31 is separated from tunneling tool 50 (208). For example, the tunneling tool 50 may be pulled in a direction away from the second portion 32 such that the tunneling tool 50 slides back through the tunnel towards incision 2 until the tool is withdrawn from the patient's tissue. If the lead 18 has been located adjacent to the target tissue, a portion of the lead may be anchored to the patient tissue. Otherwise, additional manipulation may be performed prior to anchoring the lead.

Accordingly, FIGS. 8 and 9 depict various tasks associated with placement of a medical electrical lead, catheter, medical tube, or other medical device within tissue of a patient. The numbering of the tasks does not denote a sequential ordering of the tasks. The tasks associated with the methods may be utilized to place the device in a subcutaneous tissue of the patient or in an extra-pericardial space of the patient (such as a substernal space underneath the sternum). Furthermore, a device placement procedure may utilize the tasks in both methods of FIGS. 8 and 9. For example, the method of FIG. 8 may be utilized during subcutaneous placement of the device and a subsequent substernal placement. In an alternative example, the method of FIG. 8 may be utilized during subcutaneous placement of the device with the method of FIG. 9 being utilized during a subsequent substernal placement.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. A tunneling tool system for implanting a medical electrical lead, the system comprising:
the medical electrical lead including an elongate lead body with a substantially circular cross-section, the elongate lead body including a first portion and a second portion, wherein the first portion is proximal the second portion along the length of the elongate lead body, and the second portion includes a distal end of the lead body; and
a tunneling tool comprising:
an elongate tool body formed from a resilient material and having at least a crescent-shaped segment, the elongate body having a proximal end and a distal end, and
a channel defined on an inner surface of the crescent-shaped segment and extending along a length of the crescent-shaped segment, wherein the distal end of the elongate tool body defines an opening of the channel,
wherein the first portion of the elongate lead body defines a first diameter that is less than a second diameter of the second portion of the elongate lead body, wherein the first diameter of the elongate lead body is substantially equal to or less than a width of the opening of the elongate tool body at the distal end, and wherein the second diameter of the second portion is larger than the width of the opening of the elongate tool body at the distal end,
wherein the medical electrical lead and the tunneling tool are configured such that, in a first arrangement, the first portion of the medical electrical lead is disposed with the channel, and the second portion of the medical electrical lead is disposed outside the channel beyond the distal end of the elongate tool body, wherein, in the first arrangement, the medical electrical lead engages with the elongate tool body such that movement of the elongate tool body in a distal direction along a longitudinal axis of the elongate tool body causes movement of the distal end of the lead body in the distal direction, and
wherein the medical electrical lead and the tunneling tool are configured such that, in a second arrangement, the second portion of the medical electrical lead is disposed with the channel, and the first portion of the medical electrical lead is disposed outside the channel beyond the distal end of the elongate tool body, and wherein, in the second arrangement, the medical electrical lead engages with the elongate tool body such that movement of the elongate tool body in a proximal direction along the longitudinal axis of the elongate tool body causes movement of the distal end of the lead body in the proximal direction.

2. The system of claim 1, wherein the tunneling tool is configured to releasably engage the second portion of the medical electrical lead disposed in the channel in the second arrangement.

3. The system of claim 1, wherein the crescent-shaped segment defines the opening at the distal end of the elongate tool body, wherein the opening is configured to engage the medical electrical lead in at least one of the first arrangement or the second arrangement.

4. The system of claim 1, wherein the elongate tool body further comprises a tubular segment coupled to the crescent-shaped segment.

5. The system of claim 1, further comprising a tunneling tip at the distal end of the elongate tool body.

6. The system of claim 1, further comprising a radiopaque marker element disposed on the elongate tool body, the marker element being configured to generate an indication of a location of the tool within tissue.

7. The system of claim 1, wherein the channel extends between the proximal end and the distal end of the elongate tool body.

8. The system of claim 1, further comprising a handle coupled to a proximal portion of the elongate tool body.

9. The system of claim 1, wherein, in the second arrangement, the tunneling tool is configured to pull the second portion of the medical electrical lead to advance the medical electrical lead through a subcutaneous tissue of a patient.

10. The system of claim 1, wherein, in the first arrangement, the tunneling tool is configured to push the second portion of the medical electrical lead to advance the medical electrical lead through a subcutaneous tissue of a patient.

11. The system of claim 10, wherein the distal end of the medical electrical lead defines a tunneling tip configured to tunnel through the subcutaneous tissue of the patient when the tunneling tool pushes the second portion of the medical electrical medical electrical lead in the first arrangement.

12. The system of claim 1, wherein the distal end of the elongate tool body includes projections that define the width of the opening at the distal end of the elongate tool body.

13. The system of claim 12, wherein the width of the opening defined by the projections is less than a width of the channel proximal the projections.

14. The system of claim 13, wherein the width of the channel proximal the projections is substantially equal to or greater than the diameter of the second portion.

15. The system of claim 12, wherein, when in the second arrangement, the second portion of the medical electrical lead interfaces with the projections such that the movement of the elongate tool body in the proximal direction along the longitudinal axis of the elongate tool body causes movement of the distal end of the lead body in the proximal direction.

16. The system of claim 12, wherein the width of the opening defined by the projections is substantially equal to the first diameter of the first portion of the lead.

17. The system of claim 12, wherein a friction fit is formed between the projections and the first portion of the elongate lead body.

18. The system of claim 1, wherein the medical electrical lead includes one or more electrodes along the length of the elongate lead body.

19. The system of claim 1, wherein the medical electrical lead includes an electrode defining the distal end of the lead body.

20. The system of claim 19, wherein the electrode defines a leading edge of the medical electrical lead that is configured to dissect tissue of the patient.

21. The system of claim 1, wherein, when in the first arrangement, a surface of the second portion opposes a surface of the distal end of the elongate tool body to cause movement of the distal end of the lead body in the distal direction when the elongate tool body is moved in the distal direction.

22. A method for placement of an implantable medical lead in a patient's body, the method comprising:
  forming a first incision at a first location of the body;
  inserting a first portion of the lead into the first incision;
  positioning a second portion of the lead within a channel of a tunneling tool and the first portion of the lead outside the channel; and
  guiding the lead from the first location to a second location that is spaced apart from the first location using the tunneling tool,
  wherein the implantable medical lead includes an elongate lead body with a substantially circular cross-section, the elongate lead body including the first portion and the second portion, wherein the first portion is proximal the second portion along the length of the elongate lead body, and the second portion includes a distal end of the lead body,
  wherein the tunneling tool comprises:
    an elongate tool body formed from a resilient material and having at least a crescent-shaped segment, the elongate body having a proximal end and a distal end, and
    the channel defined on an inner surface of the crescent-shaped segment and extending along a length of the crescent-shaped segment, wherein the distal end of the elongate tool body defines an opening of the channel,
  wherein the first portion of the elongate lead body defines a first diameter that is less than a second diameter of the second portion of the elongate lead body, wherein the first diameter of the elongate lead body is substantially equal to or less than a width of the opening of the elongate tool body at the distal end, and wherein the second diameter of the second portion is larger than the width of the opening of the elongate tool body at the distal end,
  wherein the medical electrical lead and the tunneling tool are configured such that, in a first arrangement, the first portion of the medical electrical lead is disposed with the channel, and the second portion of the medical electrical lead is disposed outside the channel beyond the distal end of the elongate tool body, wherein, in the first arrangement, the medical electrical lead engages with the elongate tool body such that movement of the elongate tool body in a distal direction along a longitudinal axis of the elongate tool body causes movement of the distal end of the lead body in the distal direction, and
  wherein the medical electrical lead and the tunneling tool are configured such that, in a second arrangement, the second portion of the medical electrical lead is disposed with the channel, and the first portion of the medical electrical lead is disposed outside the channel beyond the distal end of the elongate tool body, and wherein, in the second arrangement, the medical electrical lead engages with the elongate tool body such that movement of the elongate tool body in a proximal direction along the longitudinal axis of the elongate tool body causes movement of the distal end of the lead body in the proximal direction.

23. The method of claim 22, further comprising forming a second incision at the second location of the body, wherein the lead is guided from the first incision at the first location to the second incision at the second location using the tunneling tool.

24. The method of claim 22, wherein positioning the second portion of the lead comprises placing the second portion within the channel such that the first portion abuts an exterior surface of the tunneling tool at the distal end.

25. The method of claim 22, further comprising releasably engaging the lead with the tunneling tool.

26. The method of claim 25, wherein the tunneling tool comprises a tubular body having a distal opening at the distal end and the lead is configured to be releasably engaged by the distal opening.

27. The method of claim 25, wherein the first portion is formed having a detent on the elongate body of the lead such that the detent is configured to be releasably engaged by the tunneling tool.

* * * * *